United States Patent
Baril et al.

(10) Patent No.: US 12,310,620 B2
(45) Date of Patent: May 27, 2025

(54) REUSABLE SURGICAL PORT WITH DISPOSABLE SEAL ASSEMBLY

(71) Applicant: Covidien LP, Mansfield, MA (US)

(72) Inventors: Jacob Baril, Norwalk, CT (US); Justin Thomas, New Haven, CT (US); Roy Pilletere, Middletown, CT (US); Matthew Dinino, Newington, CT (US)

(73) Assignee: Covidien LP, Mansfield, MA (US)

( * ) Notice: Subject to any disclaimer, the term of this patent is extended or adjusted under 35 U.S.C. 154(b) by 212 days.

(21) Appl. No.: 17/994,810

(22) Filed: Nov. 28, 2022

(65) Prior Publication Data

US 2023/0090131 A1 Mar. 23, 2023

Related U.S. Application Data

(63) Continuation of application No. 16/564,780, filed on Sep. 9, 2019, now Pat. No. 11,523,842.

(51) Int. Cl.
*A61B 17/34* (2006.01)
*A61B 17/00* (2006.01)

(52) U.S. Cl.
CPC ...... *A61B 17/3462* (2013.01); *A61B 17/3423* (2013.01); *A61B 17/3498* (2013.01); *A61B 2017/0023* (2013.01)

(58) Field of Classification Search
CPC ............ A61B 17/3462; A61B 17/3423; A61B 17/3498; A61B 2017/0023; A61F 9/007
See application file for complete search history.

(56) References Cited

U.S. PATENT DOCUMENTS

| | | |
|---|---|---|
| 3,402,710 A | 9/1968 | Paleschuck |
| 3,495,586 A | 2/1970 | Regenbogen |
| 4,016,884 A | 4/1977 | Kwan-Gett |
| 4,112,932 A | 9/1978 | Chiulli |
| 4,183,357 A | 1/1980 | Bentley et al. |
| 4,356,826 A | 11/1982 | Kubota |
| 4,402,683 A | 9/1983 | Kopman |
| 4,653,476 A | 3/1987 | Bonnet |
| 4,737,148 A | 4/1988 | Blake |
| 4,863,430 A | 9/1989 | Klyce et al. |
| 4,863,438 A | 9/1989 | Gauderer et al. |
| 4,984,564 A | 1/1991 | Yuen |
| 5,002,557 A | 3/1991 | Hasson |

(Continued)

FOREIGN PATENT DOCUMENTS

| | | |
|---|---|---|
| CA | 2702419 A1 | 11/2010 |
| EP | 0226026 A2 | 6/1987 |

(Continued)

OTHER PUBLICATIONS

G. Ramm and A.I. Katsevich, The Radon Transform and Local Tomography, CRC Press, 1996.

(Continued)

*Primary Examiner* — Brigid K Byrd
(74) *Attorney, Agent, or Firm* — Draft Masters IP, LLC

(57) ABSTRACT

A surgical port includes a shell and a seal assembly. The shell has a housing and a cannula that extends from the housing. The housing has a sidewall defining a window therethrough. The seal assembly includes one or more seals. The seal assembly is selectively receivable into the housing through the window of the housing of the shell.

12 Claims, 10 Drawing Sheets

(56) References Cited

U.S. PATENT DOCUMENTS

| | | |
|---|---|---|
| 5,073,169 A | 12/1991 | Raiken |
| 5,082,005 A | 1/1992 | Kaldany |
| 5,122,122 A | 6/1992 | Allgood |
| 5,159,921 A | 11/1992 | Hoover |
| 5,176,697 A | 1/1993 | Hasson |
| 5,183,471 A | 2/1993 | Wilk |
| 5,192,301 A | 3/1993 | Kamiya et al. |
| 5,209,741 A | 5/1993 | Spaeth |
| 5,209,754 A | 5/1993 | Ahluwalia |
| 5,217,466 A | 6/1993 | Hasson |
| 5,242,409 A | 9/1993 | Buelna |
| 5,242,415 A | 9/1993 | Kantrowitz et al. |
| 5,257,973 A | 11/1993 | Villasuso |
| 5,257,975 A | 11/1993 | Foshee |
| 5,269,772 A | 12/1993 | Wilk |
| 5,290,249 A | 3/1994 | Foster et al. |
| 5,312,391 A | 5/1994 | Wilk |
| 5,312,417 A | 5/1994 | Wilk |
| 5,314,417 A | 5/1994 | Stephens et al. |
| 5,318,516 A | 6/1994 | Cosmescu |
| 5,330,486 A | 7/1994 | Wilk |
| 5,334,143 A | 8/1994 | Carroll |
| 5,336,169 A | 8/1994 | Divilio et al. |
| 5,336,203 A | 8/1994 | Goldhardt et al. |
| 5,337,937 A | 8/1994 | Remiszewski et al. |
| 5,345,927 A | 9/1994 | Bonutti |
| 5,360,417 A | 11/1994 | Gravener et al. |
| 5,366,478 A | 11/1994 | Brinkerhoff et al. |
| 5,375,588 A | 12/1994 | Yoon |
| 5,378,588 A | 1/1995 | Tsuchiya |
| 5,391,156 A | 2/1995 | Hildwein et al. |
| 5,394,863 A | 3/1995 | Sanford et al. |
| 5,395,367 A | 3/1995 | Wilk |
| 5,407,433 A | 4/1995 | Loomas |
| 5,437,683 A | 8/1995 | Neumann et al. |
| 5,445,615 A | 8/1995 | Yoon |
| 5,451,222 A | 9/1995 | De Maagd et al. |
| 5,458,640 A | 10/1995 | Gerrone |
| 5,460,170 A | 10/1995 | Hammerslag |
| 5,464,409 A | 11/1995 | Mohajer |
| 5,480,410 A | 1/1996 | Cuschieri et al. |
| 5,490,843 A | 2/1996 | Hildwein et al. |
| 5,507,758 A | 4/1996 | Thomason et al. |
| 5,511,564 A | 4/1996 | Wilk |
| 5,514,133 A | 5/1996 | Golub et al. |
| 5,514,153 A | 5/1996 | Bonutti |
| 5,520,698 A | 5/1996 | Koh |
| 5,522,791 A | 6/1996 | Leyva |
| 5,524,644 A | 6/1996 | Crook |
| 5,540,648 A | 7/1996 | Yoon |
| 5,545,150 A | 8/1996 | Danks et al. |
| 5,545,179 A | 8/1996 | Williamson, IV |
| 5,556,385 A | 9/1996 | Andersen |
| 5,569,159 A | 10/1996 | Anderson et al. |
| 5,577,993 A | 11/1996 | Zhu et al. |
| 5,601,581 A | 2/1997 | Fogarty et al. |
| 5,603,702 A | 2/1997 | Smith et al. |
| 5,624,399 A | 4/1997 | Ackerman |
| 5,634,911 A | 6/1997 | Hermann et al. |
| 5,634,937 A | 6/1997 | Mollenauer et al. |
| 5,643,285 A | 7/1997 | Rowden et al. |
| 5,649,550 A | 7/1997 | Crook |
| 5,651,771 A | 7/1997 | Tangherlini et al. |
| 5,653,705 A | 8/1997 | de la Torre et al. |
| 5,656,013 A | 8/1997 | Yoon |
| 5,672,168 A | 9/1997 | de la Torre et al. |
| 5,683,378 A | 11/1997 | Christy |
| 5,685,857 A | 11/1997 | Negus et al. |
| 5,697,946 A | 12/1997 | Hopper et al. |
| 5,709,675 A | 1/1998 | Williams |
| 5,713,858 A | 2/1998 | Heruth et al. |
| 5,713,869 A | 2/1998 | Morejon |
| 5,722,962 A | 3/1998 | Garcia |
| 5,728,103 A | 3/1998 | Picha et al. |
| 5,730,748 A | 3/1998 | Fogarty et al. |
| 5,735,791 A | 4/1998 | Alexander, Jr. et al. |
| 5,741,298 A | 4/1998 | MacLeod |
| 5,743,884 A * | 4/1998 | Hasson ............... A61B 17/3462 604/249 |
| 5,752,970 A | 5/1998 | Yoon |
| 5,782,817 A | 7/1998 | Franzel et al. |
| 5,795,290 A | 8/1998 | Bridges |
| 5,803,921 A | 9/1998 | Bonadio |
| 5,807,338 A | 9/1998 | Smith et al. |
| 5,810,712 A | 9/1998 | Dunn |
| 5,813,409 A | 9/1998 | Leahy et al. |
| 5,830,191 A | 11/1998 | Hildwein et al. |
| 5,836,871 A | 11/1998 | Wallace et al. |
| 5,836,913 A | 11/1998 | Orth et al. |
| 5,840,077 A | 11/1998 | Rowden et al. |
| 5,842,971 A | 12/1998 | Yoon |
| 5,848,992 A | 12/1998 | Hart et al. |
| 5,853,417 A | 12/1998 | Fogarty et al. |
| 5,857,461 A | 1/1999 | Levitsky et al. |
| 5,865,817 A | 2/1999 | Moenning et al. |
| 5,871,474 A | 2/1999 | Hermann et al. |
| 5,876,413 A | 3/1999 | Fogarty et al. |
| 5,894,843 A | 4/1999 | Benetti et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,914,415 A | 6/1999 | Tago |
| 5,916,198 A | 6/1999 | Dillow |
| 5,941,898 A | 8/1999 | Moenning et al. |
| 5,951,588 A | 9/1999 | Moenning |
| 5,957,913 A | 9/1999 | de la Torre et al. |
| 5,964,781 A | 10/1999 | Mollenauer et al. |
| 5,976,174 A | 11/1999 | Ruiz |
| 5,997,515 A | 12/1999 | de la Torre et al. |
| 6,017,355 A | 1/2000 | Hessel et al. |
| 6,018,094 A | 1/2000 | Fox |
| 6,024,736 A | 2/2000 | de la Torre et al. |
| 6,030,402 A | 2/2000 | Thompson et al. |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| 6,059,816 A | 5/2000 | Moenning |
| 6,068,639 A | 5/2000 | Fogarty et al. |
| 6,077,288 A | 6/2000 | Shimomura et al. |
| 6,086,603 A | 7/2000 | Termin et al. |
| 6,093,176 A | 7/2000 | Dennis |
| 6,099,506 A | 8/2000 | Macoviak et al. |
| 6,110,154 A | 8/2000 | Shimomura et al. |
| 6,142,936 A | 11/2000 | Beane et al. |
| 6,156,006 A | 12/2000 | Brosens et al. |
| 6,162,196 A | 12/2000 | Hart et al. |
| 6,171,282 B1 | 1/2001 | Ragsdale |
| 6,197,002 B1 | 3/2001 | Peterson |
| 6,217,555 B1 | 4/2001 | Hart et al. |
| 6,228,063 B1 | 5/2001 | Aboul-Hosn |
| 6,234,958 B1 | 5/2001 | Snoke et al. |
| 6,238,373 B1 | 5/2001 | de la Torre et al. |
| 6,241,768 B1 | 6/2001 | Agarwal et al. |
| 6,251,119 B1 | 6/2001 | Addis |
| 6,254,534 B1 | 7/2001 | Butler et al. |
| 6,264,604 B1 | 7/2001 | Kieturakis et al. |
| 6,276,661 B1 | 8/2001 | Laird |
| 6,293,952 B1 | 9/2001 | Brosens et al. |
| 6,315,770 B1 | 11/2001 | de la Torre et al. |
| 6,319,246 B1 | 11/2001 | de la Torre et al. |
| 6,328,720 B1 | 12/2001 | McNally et al. |
| 6,329,637 B1 | 12/2001 | Hembree et al. |
| 6,371,968 B1 | 4/2002 | Kogasaka et al. |
| 6,382,211 B1 | 5/2002 | Crook |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |

(56) References Cited

U.S. PATENT DOCUMENTS

| | | |
|---|---|---|
| 6,468,292 B1 | 10/2002 | Mollenauer et al. |
| 6,485,410 B1 | 11/2002 | Loy |
| 6,488,620 B1 | 12/2002 | Segermark et al. |
| 6,488,692 B1 | 12/2002 | Spence et al. |
| 6,524,283 B1 | 2/2003 | Hopper et al. |
| 6,527,787 B1 | 3/2003 | Fogarty et al. |
| 6,544,210 B1 | 4/2003 | Trudel et al. |
| 6,551,270 B1 | 4/2003 | Bimbo et al. |
| 6,558,371 B2 | 5/2003 | Dorn |
| 6,562,022 B2 | 5/2003 | Hoste et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,684,405 B2 | 2/2004 | Ezdey |
| 6,706,050 B1 | 3/2004 | Giannadakis |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,064 B2 | 6/2007 | Hopper et al. |
| 7,235,084 B2 | 6/2007 | Skakoon et al. |
| 7,238,154 B2 | 7/2007 | Ewers et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |
| 7,481,765 B2 | 1/2009 | Ewers et al. |
| 7,493,703 B2 | 2/2009 | Kim et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,625,361 B2 | 12/2009 | Suzuki et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,753,901 B2 | 7/2010 | Piskun et al. |
| 7,758,500 B2 | 7/2010 | Boyd et al. |
| 7,762,995 B2 | 7/2010 | Eversull et al. |
| 7,766,824 B2 | 8/2010 | Jensen et al. |
| 7,787,963 B2 | 8/2010 | Geistert et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,846,123 B2 | 12/2010 | Vassiliades et al. |
| 7,850,600 B1 | 12/2010 | Piskun |
| 7,850,667 B2 | 12/2010 | Gresham |
| 7,867,164 B2 | 1/2011 | Butler et al. |
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,913,697 B2 | 3/2011 | Nguyen et al. |
| 7,951,076 B2 | 5/2011 | Hart et al. |
| 7,955,257 B2 | 6/2011 | Frasier et al. |
| 7,955,313 B2 | 6/2011 | Boismier |
| 7,998,068 B2 | 8/2011 | Bonadio et al. |
| 8,021,296 B2 | 9/2011 | Bonadio et al. |
| 8,025,670 B2 | 9/2011 | Sharp et al. |
| 8,038,652 B2 | 10/2011 | Morrison et al. |
| 8,066,673 B2 | 11/2011 | Hart et al. |
| 8,079,986 B2 | 12/2011 | Taylor et al. |
| 8,092,430 B2 | 1/2012 | Richard et al. |
| 8,105,234 B2 | 1/2012 | Ewers et al. |
| 8,109,873 B2 | 2/2012 | Albrecht et al. |
| 8,157,786 B2 | 4/2012 | Miller et al. |
| 8,157,817 B2 | 4/2012 | Bonadio et al. |
| 8,187,177 B2 | 5/2012 | Kahle et al. |
| 8,187,178 B2 | 5/2012 | Bonadio et al. |
| 8,241,209 B2 | 8/2012 | Shelton, IV et al. |
| 8,262,568 B2 | 9/2012 | Albrecht et al. |
| 8,323,184 B2 | 12/2012 | Spiegal et al. |
| 8,335,783 B2 | 12/2012 | Milby |
| 8,343,047 B2 | 1/2013 | Albrecht et al. |
| 8,353,824 B2 | 1/2013 | Shelton, IV et al. |
| 8,403,889 B2 | 3/2013 | Richard |
| 8,480,683 B2 | 7/2013 | Fowler et al. |
| 8,574,153 B2 | 11/2013 | Richard |
| 8,585,632 B2 | 11/2013 | Okoniewski |
| 8,828,023 B2 | 9/2014 | Neff et al. |

(56) References Cited

U.S. PATENT DOCUMENTS

| | | |
|---|---|---|
| 11,523,842 B2 | 12/2022 | Baril et al. |
| 2001/0037053 A1 | 11/2001 | Bonadio et al. |
| 2002/0055714 A1 | 5/2002 | Rothschild |
| 2003/0014076 A1 | 1/2003 | Mollenauer et al. |
| 2003/0093104 A1 | 5/2003 | Bonner et al. |
| 2003/0187376 A1 | 10/2003 | Rambo |
| 2003/0233115 A1 | 12/2003 | Eversull et al. |
| 2003/0236549 A1 | 12/2003 | Bonadio et al. |
| 2004/0059297 A1 | 3/2004 | Racenet et al. |
| 2004/0092795 A1 | 5/2004 | Bonadio et al. |
| 2004/0102804 A1 | 5/2004 | Chin |
| 2004/0111061 A1 | 6/2004 | Curran |
| 2004/0138529 A1 | 7/2004 | Wiltshire et al. |
| 2004/0204734 A1 | 10/2004 | Wagner et al. |
| 2004/0267096 A1 | 12/2004 | Caldwell et al. |
| 2005/0020884 A1 | 1/2005 | Hart et al. |
| 2005/0070935 A1 | 3/2005 | Ortiz |
| 2005/0096695 A1 | 5/2005 | Olich |
| 2005/0119525 A1 | 6/2005 | Takemoto |
| 2005/0137459 A1 | 6/2005 | Chin et al. |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2005/0209608 A1 | 9/2005 | O'Heeron |
| 2005/0222582 A1 | 10/2005 | Wenchell |
| 2005/0245876 A1 | 11/2005 | Khosravi et al. |
| 2005/0251092 A1 | 11/2005 | Howell et al. |
| 2005/0277946 A1 | 12/2005 | Greenhalgh |
| 2006/0071432 A1 | 4/2006 | Staudner |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0212063 A1 | 9/2006 | Wilk |
| 2006/0224161 A1 | 10/2006 | Bhattacharyya |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0270911 A1 | 11/2006 | Voegele et al. |
| 2007/0088277 A1 | 4/2007 | McGinley et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0203398 A1 | 8/2007 | Bonadio et al. |
| 2007/0208312 A1 | 9/2007 | Norton et al. |
| 2007/0225650 A1 | 9/2007 | Hart et al. |
| 2007/0270654 A1 | 11/2007 | Pignato et al. |
| 2007/0270882 A1 | 11/2007 | Hjelle et al. |
| 2008/0009826 A1 | 1/2008 | Miller et al. |
| 2008/0021360 A1 | 1/2008 | Fihe et al. |
| 2008/0027476 A1 | 1/2008 | Piskun |
| 2008/0048011 A1 | 2/2008 | Weller |
| 2008/0091143 A1 | 4/2008 | Taylor et al. |
| 2008/0097162 A1 | 4/2008 | Bonadio et al. |
| 2008/0097332 A1 | 4/2008 | Greenhalgh et al. |
| 2008/0119868 A1 | 5/2008 | Sharp et al. |
| 2008/0161826 A1 | 7/2008 | Guiraudon |
| 2008/0188868 A1 | 8/2008 | Weitzner et al. |
| 2008/0194973 A1 | 8/2008 | Imam |
| 2008/0200767 A1 | 8/2008 | Ewers et al. |
| 2008/0255519 A1 | 10/2008 | Piskun et al. |
| 2008/0319261 A1 | 12/2008 | Lucini et al. |
| 2009/0012477 A1 | 1/2009 | Norton et al. |
| 2009/0036738 A1 | 2/2009 | Cuschieri et al. |
| 2009/0036745 A1 | 2/2009 | Bonadio et al. |
| 2009/0093752 A1 | 4/2009 | Richard et al. |
| 2009/0093850 A1 | 4/2009 | Richard |
| 2009/0105635 A1 | 4/2009 | Bettuchi et al. |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0182288 A1 | 7/2009 | Spenciner |
| 2009/0187079 A1 | 7/2009 | Albrecht et al. |
| 2009/0204067 A1 | 8/2009 | Abu-Halawa |
| 2009/0221968 A1 | 9/2009 | Morrison et al. |
| 2009/0227843 A1 | 9/2009 | Smith et al. |
| 2009/0326330 A1 | 12/2009 | Bonadio et al. |
| 2009/0326332 A1 | 12/2009 | Carter |
| 2010/0063452 A1 | 3/2010 | Edelman et al. |
| 2010/0100043 A1 | 4/2010 | Racenet |
| 2010/0113886 A1 | 5/2010 | Piskun et al. |
| 2010/0228094 A1 | 9/2010 | Ortiz et al. |
| 2010/0240960 A1 | 9/2010 | Richard |
| 2010/0249516 A1 | 9/2010 | Shelton, IV et al. |
| 2010/0249523 A1 | 9/2010 | Spiegal et al. |
| 2010/0249524 A1 | 9/2010 | Ransden et al. |
| 2010/0262080 A1 | 10/2010 | Shelton, IV et al. |
| 2010/0280326 A1 | 11/2010 | Hess et al. |
| 2010/0286484 A1 | 11/2010 | Stellon et al. |
| 2010/0286506 A1 | 11/2010 | Ransden et al. |
| 2010/0298646 A1 | 11/2010 | Stellon et al. |
| 2010/0312063 A1 | 12/2010 | Hess et al. |
| 2011/0009704 A1 | 1/2011 | Marczyk et al. |
| 2011/0021877 A1 | 1/2011 | Fortier et al. |
| 2011/0028891 A1 | 2/2011 | Okoniewski |
| 2011/0034778 A1 | 2/2011 | Kleyman |
| 2011/0054257 A1 | 3/2011 | Stopek |
| 2011/0054258 A1 | 3/2011 | O'Keefe et al. |
| 2011/0054260 A1 | 3/2011 | Albrecht et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0118553 A1 | 5/2011 | Stopek |
| 2011/0124968 A1 | 5/2011 | Kleyman |
| 2011/0124969 A1 | 5/2011 | Stopek |
| 2011/0124970 A1 | 5/2011 | Kleyman |
| 2011/0125186 A1 | 5/2011 | Fowler et al. |
| 2011/0166423 A1 | 7/2011 | Farascioni et al. |
| 2011/0251463 A1 | 10/2011 | Kleyman |
| 2011/0251464 A1 | 10/2011 | Kleyman |
| 2011/0251465 A1 | 10/2011 | Kleyman |
| 2011/0251466 A1 | 10/2011 | Kleyman et al. |
| 2011/0282160 A1* | 11/2011 | Bhadri .................. A61B 1/313 |
| | | 600/236 |
| 2011/0313250 A1 | 12/2011 | Kleyman |
| 2012/0004613 A1* | 1/2012 | Franer .................... B65B 55/12 |
| | | 604/167.03 |
| 2012/0059640 A1 | 3/2012 | Roy et al. |
| 2012/0130177 A1 | 5/2012 | Davis |
| 2012/0130181 A1 | 5/2012 | Davis |
| 2012/0130182 A1 | 5/2012 | Rodrigues, Jr. et al. |
| 2012/0130183 A1 | 5/2012 | Barnes |
| 2012/0130184 A1 | 5/2012 | Richard |
| 2012/0130185 A1 | 5/2012 | Pribanic |
| 2012/0130186 A1 | 5/2012 | Stopek et al. |
| 2012/0130187 A1 | 5/2012 | Okoniewski |
| 2012/0130188 A1 | 5/2012 | Okoniewski |
| 2012/0130190 A1 | 5/2012 | Kasvikis |
| 2012/0130191 A1 | 5/2012 | Pribanic |
| 2012/0149987 A1 | 6/2012 | Richard et al. |
| 2012/0149988 A1* | 6/2012 | Hickingbotham .......................... |
| | | A61B 17/3462 |
| | | 600/208 |
| 2012/0157777 A1 | 6/2012 | Okoniewski |
| 2012/0157779 A1 | 6/2012 | Fischvogt |
| 2012/0157780 A1 | 6/2012 | Okoniewski et al. |
| 2012/0157781 A1 | 6/2012 | Kleyman |
| 2012/0157782 A1 | 6/2012 | Alfieri |
| 2012/0157783 A1 | 6/2012 | Okoniewski et al. |
| 2012/0157784 A1 | 6/2012 | Kleyman et al. |
| 2012/0157785 A1 | 6/2012 | Kleyman |
| 2012/0157786 A1 | 6/2012 | Pribanic |
| 2012/0190931 A1 | 7/2012 | Stopek |
| 2012/0190932 A1 | 7/2012 | Okoniewski |
| 2012/0190933 A1 | 7/2012 | Kleyman |
| 2012/0209077 A1 | 8/2012 | Racenet |
| 2012/0209078 A1 | 8/2012 | Pribanic et al. |
| 2012/0245427 A1 | 9/2012 | Kleyman |

(56) References Cited

U.S. PATENT DOCUMENTS

| | | |
|---|---|---|
| 2012/0245429 A1 | 9/2012 | Smith |
| 2012/0245430 A1 | 9/2012 | Kleyman et al. |
| 2012/0283520 A1 | 11/2012 | Kleyman |
| 2013/0225930 A1 | 8/2013 | Smith |
| 2013/0225931 A1 | 8/2013 | Cruz et al. |
| 2013/0245373 A1 | 9/2013 | Okoniewski |
| 2013/0274559 A1 | 10/2013 | Fowler et al. |
| 2013/0310651 A1 | 11/2013 | Alfieri |
| 2014/0018632 A1 | 1/2014 | Kleyman |
| 2018/0116693 A1 | 5/2018 | Blanchard |

FOREIGN PATENT DOCUMENTS

| | | |
|---|---|---|
| EP | 0538060 A1 | 4/1993 |
| EP | 0567142 A2 | 10/1993 |
| EP | 0577400 A1 | 1/1994 |
| EP | 0630660 A1 | 12/1994 |
| EP | 0807416 A2 | 11/1997 |
| EP | 0950376 A1 | 10/1999 |
| EP | 1188415 A2 | 3/2002 |
| EP | 1312318 A1 | 5/2003 |
| EP | 1774918 A1 | 4/2007 |
| EP | 1932485 A1 | 6/2008 |
| EP | 2044889 A1 | 4/2009 |
| EP | 2044897 A1 | 4/2009 |
| EP | 2080494 A1 | 7/2009 |
| EP | 2095781 A2 | 9/2009 |
| EP | 2098182 A2 | 9/2009 |
| EP | 2138117 A1 | 12/2009 |
| EP | 2138118 A2 | 12/2009 |
| EP | 2181657 A2 | 5/2010 |
| EP | 2226025 A1 | 9/2010 |
| EP | 2229900 A1 | 9/2010 |
| EP | 2238924 A1 | 10/2010 |
| EP | 2238925 A1 | 10/2010 |
| EP | 2238926 A2 | 10/2010 |
| EP | 2238933 A1 | 10/2010 |
| EP | 2248478 A1 | 11/2010 |
| EP | 2248482 A1 | 11/2010 |
| EP | 2253283 A1 | 11/2010 |
| EP | 2272450 A2 | 1/2011 |
| EP | 2277464 A1 | 1/2011 |
| EP | 2289438 A1 | 3/2011 |
| EP | 2292165 | 3/2011 |
| EP | 2343019 | 7/2011 |
| GB | 2469083 | 4/2009 |
| JP | 05-293112 A | 11/1993 |
| JP | 10-501711 A | 2/1998 |
| JP | 2006280959 A | 10/2006 |
| JP | 2008057056 A | 3/2008 |
| WO | 84/01512 A1 | 4/1984 |
| WO | 9314801 | 8/1993 |
| WO | 9404067 | 3/1994 |
| WO | 9532019 A1 | 11/1995 |
| WO | 9610963 A1 | 4/1996 |
| WO | 9636283 | 11/1996 |
| WO | 9733520 A1 | 9/1997 |
| WO | 9742889 A1 | 11/1997 |
| WO | WO9747248 A1 | 12/1997 |
| WO | 9916368 | 4/1999 |
| WO | 9922804 | 5/1999 |
| WO | 9929250 | 6/1999 |
| WO | 9952577 A1 | 10/1999 |
| WO | 0032116 | 6/2000 |
| WO | 0032120 | 6/2000 |
| WO | 0054675 | 9/2000 |
| WO | 0108581 | 2/2001 |
| WO | 0149363 | 7/2001 |
| WO | 0207611 | 1/2002 |
| WO | 03034908 A2 | 5/2003 |
| WO | 03071926 | 9/2003 |
| WO | 03077726 | 9/2003 |
| WO | 2004043275 | 5/2004 |
| WO | 2004054456 | 7/2004 |
| WO | 2004075741 A2 | 9/2004 |
| WO | 2004075930 A2 | 9/2004 |
| WO | 2005058409 | 6/2005 |
| WO | 2006019723 | 2/2006 |
| WO | 2006100658 A2 | 9/2006 |
| WO | 2006110733 | 10/2006 |
| WO | 2007018458 | 2/2007 |
| WO | 2007095703 | 8/2007 |
| WO | 2007143200 | 12/2007 |
| WO | 2008015566 A2 | 2/2008 |
| WO | 2008042005 | 4/2008 |
| WO | 2008077080 | 6/2008 |
| WO | 2008093313 | 8/2008 |
| WO | 2008103151 | 8/2008 |
| WO | 2008121294 A1 | 10/2008 |
| WO | 2008147644 | 12/2008 |
| WO | 2009036343 | 3/2009 |
| WO | 2010000047 | 1/2010 |
| WO | 2010141409 A1 | 12/2010 |
| WO | 2010141673 | 12/2010 |
| WO | 2016025132 A1 | 2/2016 |

OTHER PUBLICATIONS

F. Natterer, The Mathematics of Computerized Tomography, Wiley, 1989.
G.T. Herman et al., Basic Methods of Tomography and Inverse Problems, Hildger, 1987.
G.T. Herman and Attila Kuba, Discrete Tomography, Birhauser, 1999.
Extended European Search Report for application No. 20195301.5 dated Jan. 28, 2021.
European Communication for application No. 20 195 301 .5 dated Nov. 21, 2022.
Extended European Search Report issued in corresponding European Application No. 23212710.0 dated Feb. 19, 2024, 6 pages.
JP2020-133609, Notice of Reasons for Rejection, May 1, 2024, 8 pgs.
Japanese Notice of Allowance, 2020-133609, Oct. 7, 2024, 5 pgs.

* cited by examiner

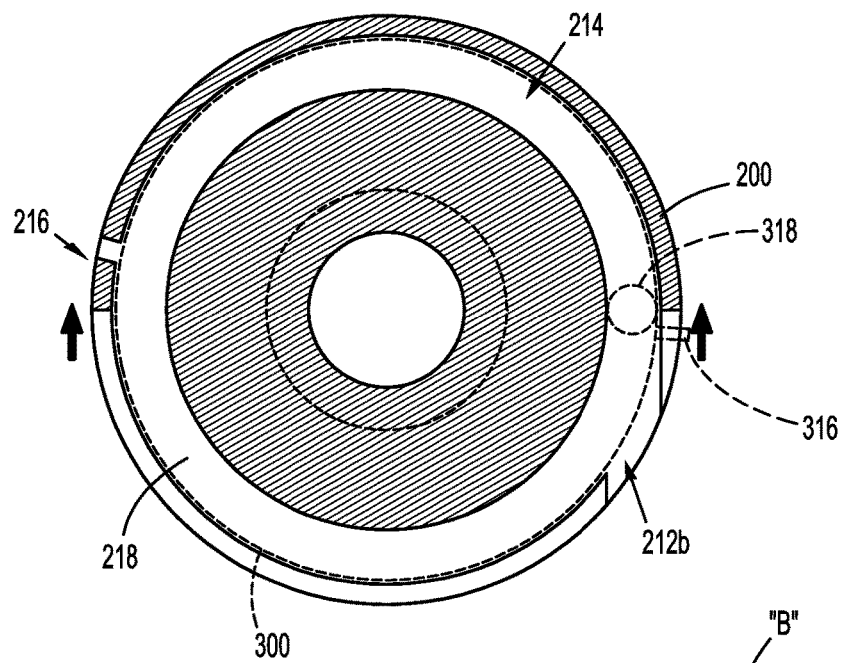
FIG. 11
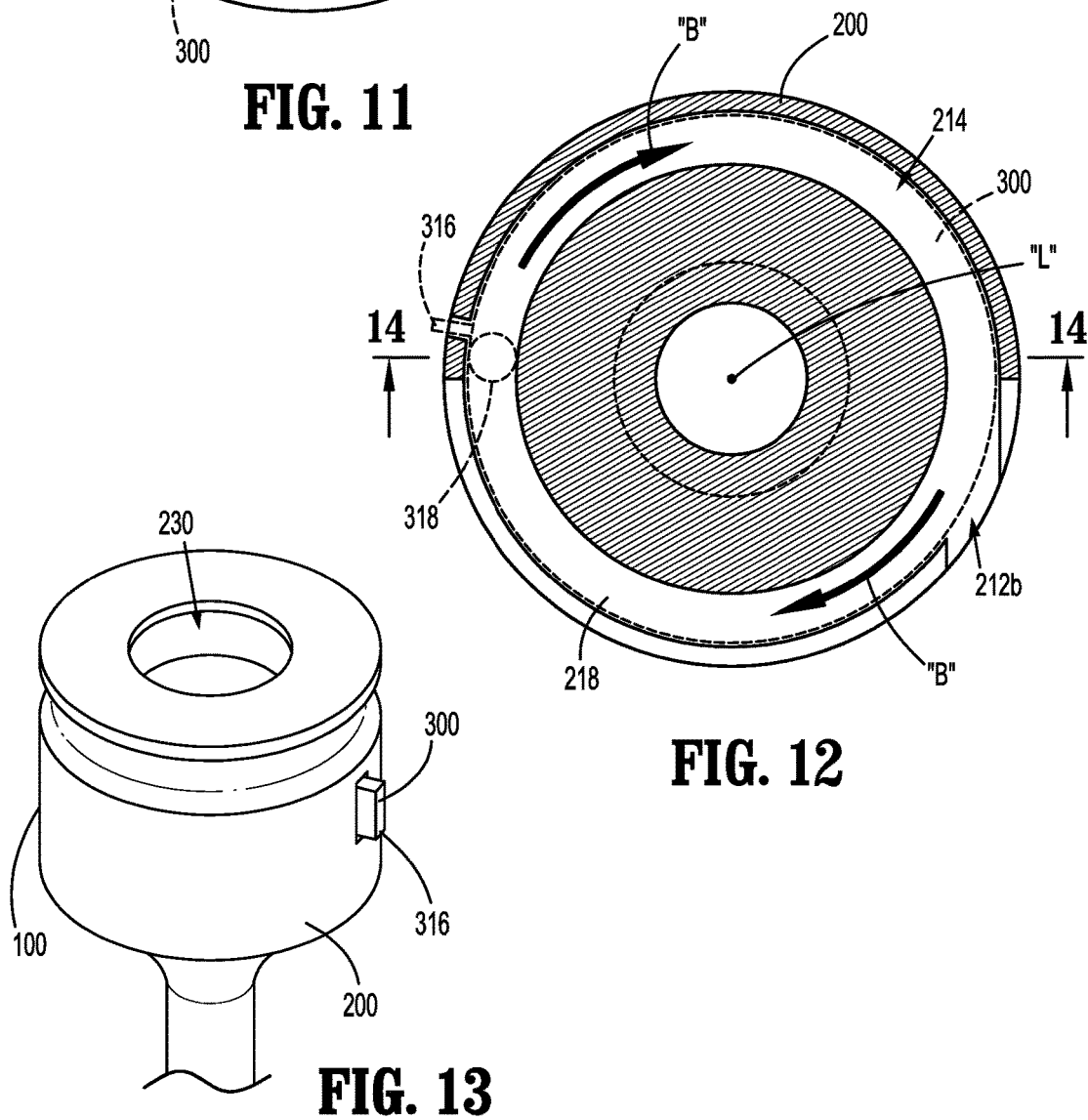
FIG. 12
FIG. 13

REUSABLE SURGICAL PORT WITH DISPOSABLE SEAL ASSEMBLY

CROSS REFERENCE TO RELATED APPLICATIONS

This application is a continuation of U.S. patent application Ser. No. 16/564,780, filed Sep. 9, 2019, the entire contents of which are incorporated by reference herein.

TECHNICAL FIELD

This disclosure relates generally to surgical instruments, and in particular, to surgical ports with reusable and/or disposable components for use during a minimally invasive surgical procedure such as a robotic surgical procedure.

BACKGROUND

Robotic surgical systems have been used in minimally invasive medical procedures. Some robotic surgical systems include a robot arm having an instrument drive assembly coupled thereto for coupling surgical instruments to the robot arm, such as, for example, a pair of jaw members, electrosurgical forceps, cutting instruments, or any other endoscopic or open surgical devices, and a mount assembly coupled thereto for coupling surgical accessories to the robot arm, such as, for example, a trocar or surgical port, an optical device, or the like.

Prior to or during use of the robotic system, surgical instruments are selected and connected to the instrument drive assembly of each robot arm, where the instrument drive assembly can drive the actuation of an end effector of the surgical instrument. Under certain procedures, a surgical accessory, such as, for example, an optical device or a surgical port may be coupled to the robot arm via the mount assembly of the robot arm. During a procedure, the end effector and/or a portion of the surgical instrument may be inserted through the surgical port, and a small incision or a natural orifice of a patient, to bring the end effector proximate a working site within the body of the patient. Such surgical ports may provide additional stability, and act as a guide channel, for the surgical instrument during insertion and actuation of the end effector.

Given the loads and torques that can be applied during robotic surgery, high strength surgical ports are required to provide additional functionality. Surgical ports made from plastic material may not be sufficiently durable for high torques applied by surgical robot arms, but metallic components are expensive.

SUMMARY

This disclosure is directed to a surgical port system having a shell and a disposable seal assembly that is selectively receivable and/or removable to/from the shell. The shell may be 3D printed. In embodiments, the shell may include titanium. The shell can be configured to be lightweight, yet withstand high loads. The disposable seal assembly, which may be in the form of a puck, can include plastic and/or rubber material designed to seal against the shell and internally to enable access via laparoscopic instruments advanced through the seal assembly and shell. The shell may define a window through which the seal assembly passes. The seal assembly is configured to rotate within, and relative to the shell, for camming along the shell to snap-fit to the shell. With the seal assembly secured to the shell via snap-fit, the seal assembly is sealed against the shell and internally against the instruments passed therethrough. The seal assembly can be removed from the shell and discarded, for instance, after a surgical procedure. With the seal assembly removed, the shell can be sterilized for reprocessing and reuse with another seal assembly.

According to one aspect, this disclosure is directed to a surgical port including a shell and a seal assembly. The shell has a housing and a cannula that extends from the housing. The housing has a sidewall defining a window therethrough. The seal assembly includes one or more seals. The seal assembly is selectively receivable into the housing through the window of the housing of the shell.

In embodiments, the seal assembly may be selectively rotatable relative to the shell to secure the seal assembly to the shell. The seal assembly may be selectively removable from the shell.

In various embodiments, the shell may include reusable material and the seal assembly may include disposable material. The shell may include titanium and the seal assembly may include plastic and/or rubber.

In many embodiments, the seal assembly may include a floating seal and a duckbill seal.

In embodiments, the seal assembly may include a detent and the shell may define a detent slot that is positioned to receive the detent for securing the seal assembly to the shell.

In various embodiments, the seal assembly may support a gasket to seal the seal assembly within the shell.

In some embodiments, the seal assembly may include a seal housing having a first geometry. The window may have a second geometry. The first geometry may be keyed to the second geometry. The seal housing may include a tooth and the window may include a tooth gap positioned to receive the tooth when the seal housing is laterally slid into the window.

According to another aspect, this disclosure is directed to a surgical port system. The surgical port system includes a first seal assembly including one or more seals, a second seal assembly including one or more seals, and a shell. The shell has a housing and a cannula that extends from the housing. The housing has a sidewall defining a window therethrough that is configured to receive the first and second seal assemblies therethrough so that the shell can support one of the first or second seal assemblies therein at any given time.

In embodiments, each of the first and second seal assemblies may be selectively rotatable relative to the shell to secure the respective first or second seal assembly to the shell. The respective first or second seal assembly may be selectively removable from the shell.

In various embodiments, the shell may include reusable material and each of the first and second seal assemblies may include disposable material. The shell may include titanium and each of the first and second seal assemblies may include at least one of plastic or rubber.

In some embodiments, at least one of the first or second seal assemblies may include a floating seal and a duckbill seal.

In many embodiments, each of the first and second seal assemblies may include a detent and the shell may define a detent slot that is positioned to receive the detent for securing one of the first or second seal assemblies to the shell.

In embodiments, each of the first and second seal assemblies may support a gasket to seal one of the first or second seal assemblies within the shell.

In some embodiments, each of the first and second seal assemblies may include a tooth and the window of the shell may include a tooth gap positioned to receive the teeth of the first and second seal assemblies.

According to yet another aspect, this disclosure is directed to a method for sealing surgical instrumentation with a surgical port system. The method includes inserting a first disposable seal assembly through a window defined in a sidewall of a housing of a shell, the shell including a cannula that extends from the housing. The method further includes rotating the first disposable seal assembly relative to the housing to secure the first disposable seal assembly to the shell for providing a surgical port assembly that enables surgical instrumentation to remain sealed when such surgical instrumentation is advanced through surgical port assembly. The method also includes selectively removing the first disposable seal assembly from the housing for selective replacement with a second disposable seal assembly receivable through the window of the housing.

The details of one or more aspects of this disclosure are set forth in the accompanying drawings and the description below. Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with the detailed description of the embodiments given below, serve to explain the principles of the disclosure.

FIGS. 9-13 are progressive views illustrating the seal assembly of FIG. 3 being secured to the shell of FIG. 4.

DETAILED DESCRIPTION

Figure 1:
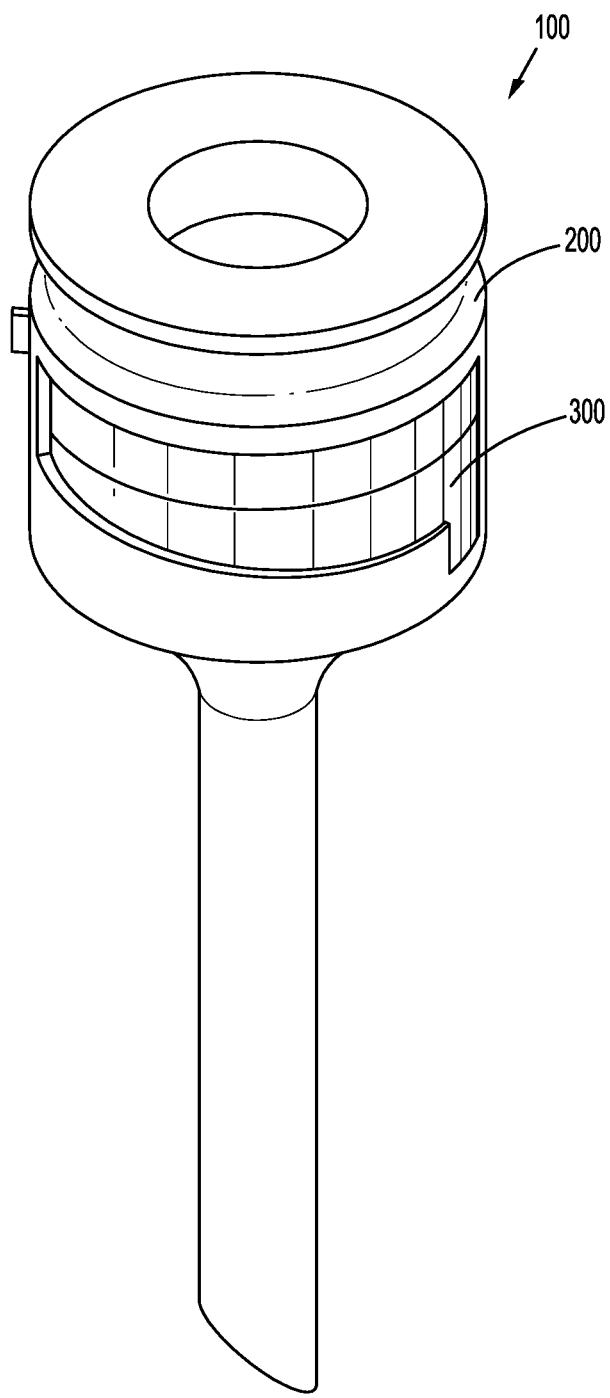
FIG. 1 is a perspective view of a surgical port system.
Figure 2:
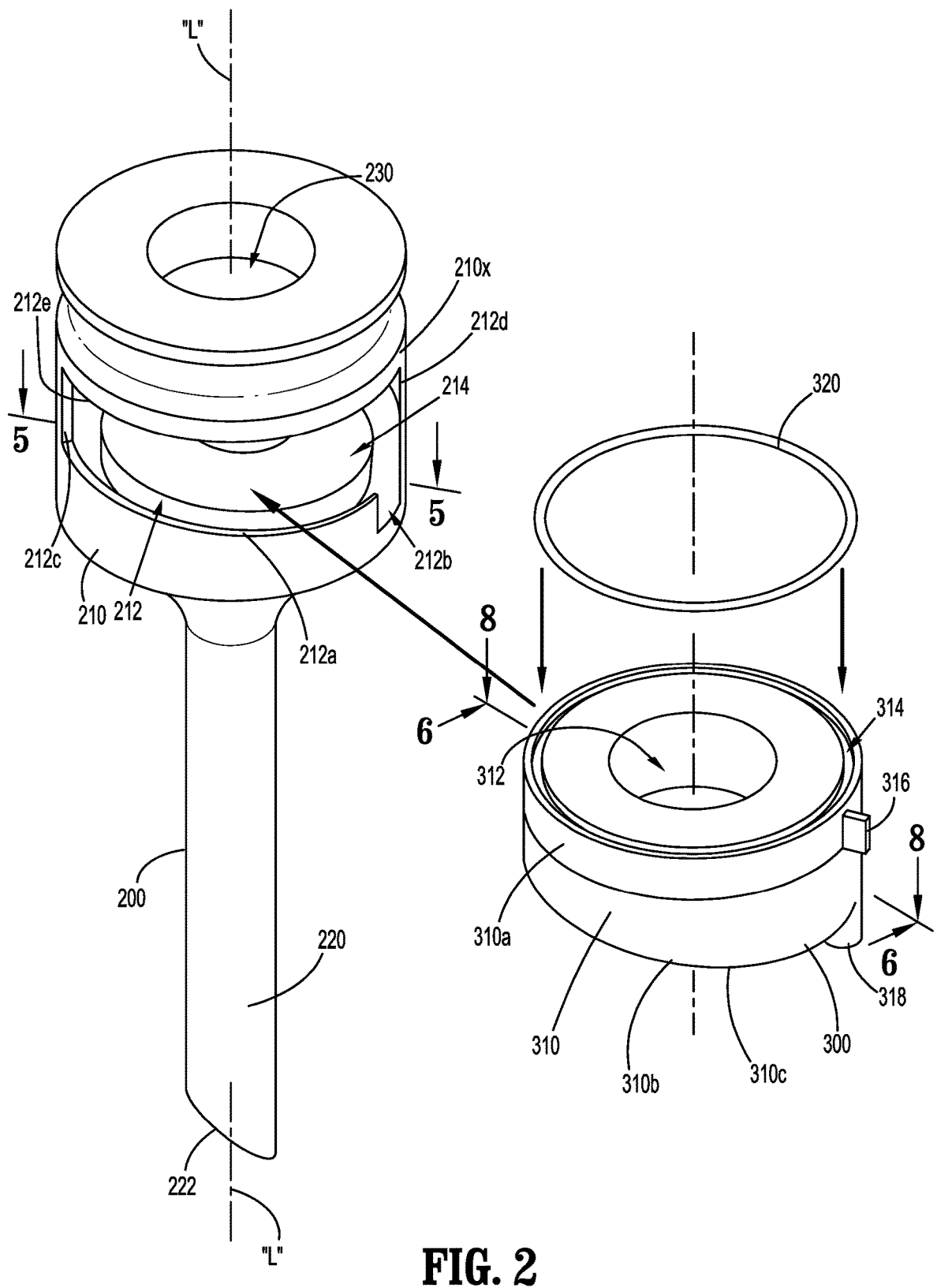
FIG. 2 is a perspective view, with parts separated, of the surgical port system of FIG. 1.

Aspects of this disclosure are described in detail with reference to the drawings, in which like reference numerals designate identical or corresponding elements in each of the several views. Additionally, the term "proximal" or "trailing" refers to the portion of structure that is closer to the clinician and the term "distal" or "leading" refers to the portion of structure that is farther from the clinician. As commonly known, the term "clinician" refers to a doctor (e.g., a surgeon), a nurse, or any other care provider and may include support personnel.

In the following description, well-known functions or constructions are not described in detail to avoid obscuring this disclosure in unnecessary detail.

With regard to FIG. 1, a surgical port system 100 is a multi-piece construct including a shell 200, which may be autoclavable and reusable, and a seal assembly 300 that is selectively removable from shell 200, and which may be disposable when removed from shell 200. Shell 200 may include any suitable material such as metallic material like titanium. Seal assembly 300 may include any suitable material such as a plastic and/or rubber.

Turning to FIGS. 2-8, shell 200 of surgical port system 100 includes a housing 210 supported on a trailing end portion of shell 200 and an elongated cannula 220 that extends distally from housing 210 to an insertion tip 222 on a leading end portion of cannula 220. Shell 200 defines a longitudinal axis "L" and a central passage 230 that extends distally along longitudinal axis "L" from a proximal end portion of housing 210 through a distal end portion of insertion tip 222 of cannula 220 for receiving surgical instrumentation (not shown) therethrough. Such surgical instrumentation can include graspers, forceps, staplers, endoscopes, clip appliers, stitching devices, etc. Housing 210 defines a window 212 through a sidewall 210x of housing 210 that is keyed to seal assembly 300 for receiving seal assembly 300 within an inner cavity 214 defined by housing 210. Window 212 is defined by an angled bottom edge 212a having a tooth gap 212b, a first side edge 212c extending from a first side of angled bottom edge 212a, a second side edge 212d extending from tooth gap 212b on a second side of angled bottom edge 212a, and a top edge 212e that connects first and second side edges 212c, 212d. Housing 210 further defines a detent slot 216 that is angularly offset from window 212 of housing 210 for coupling seal assembly 300 to shell 200. Housing 210 also includes a keyed track 218 along which seal assembly 200 is configured to cam toward detent slot 216 of housing 210.

Seal assembly 300 of surgical port system 100 includes a seal housing 310 and a gasket 320 (e.g., an O-ring) supported by housing 310. Seal housing 310 defines an opening 312 that extends longitudinally through seal housing 310 and a gasket channel 314 that extends around an upper surface of seal housing 310 for selectively receiving gasket 320 therein. Seal housing 310 can include an upper housing 310a and a lower housing 310b that can be integrally (e.g., monolithically) formed together as a unit or independent portions of seal housing 310 that can be selectively secured together using any suitable securement technique such as fastening, welding, adhesion, snap-fit, friction-fit, etc., or combinations thereof. Seal housing 310 has geometry that is keyed to window 212 of housing 210 of shell 200 and configured to be received within inner cavity 214 of housing 210 of shell 200 through window 212 of housing 210 of shell 200. Seal housing 310 of seal assembly 300 includes an angled bottom edge 310c that corresponds to angled bottom edge 212a of housing 210 of shell 200. Seal housing 310 further includes a detent 316 that extends radially outward from an outer side surface of seal housing 310 and is configured to move toward and away from outer side surface of seal housing 310 (e.g., by flexing) for selectively engaging detent slot 216 of housing 210 of shell 200. In some embodiments, detent 316 may be formed of any suitable flexible material. Seal housing 310 further includes a tooth 318 that depends distally from seal housing 310.

Figure 3:
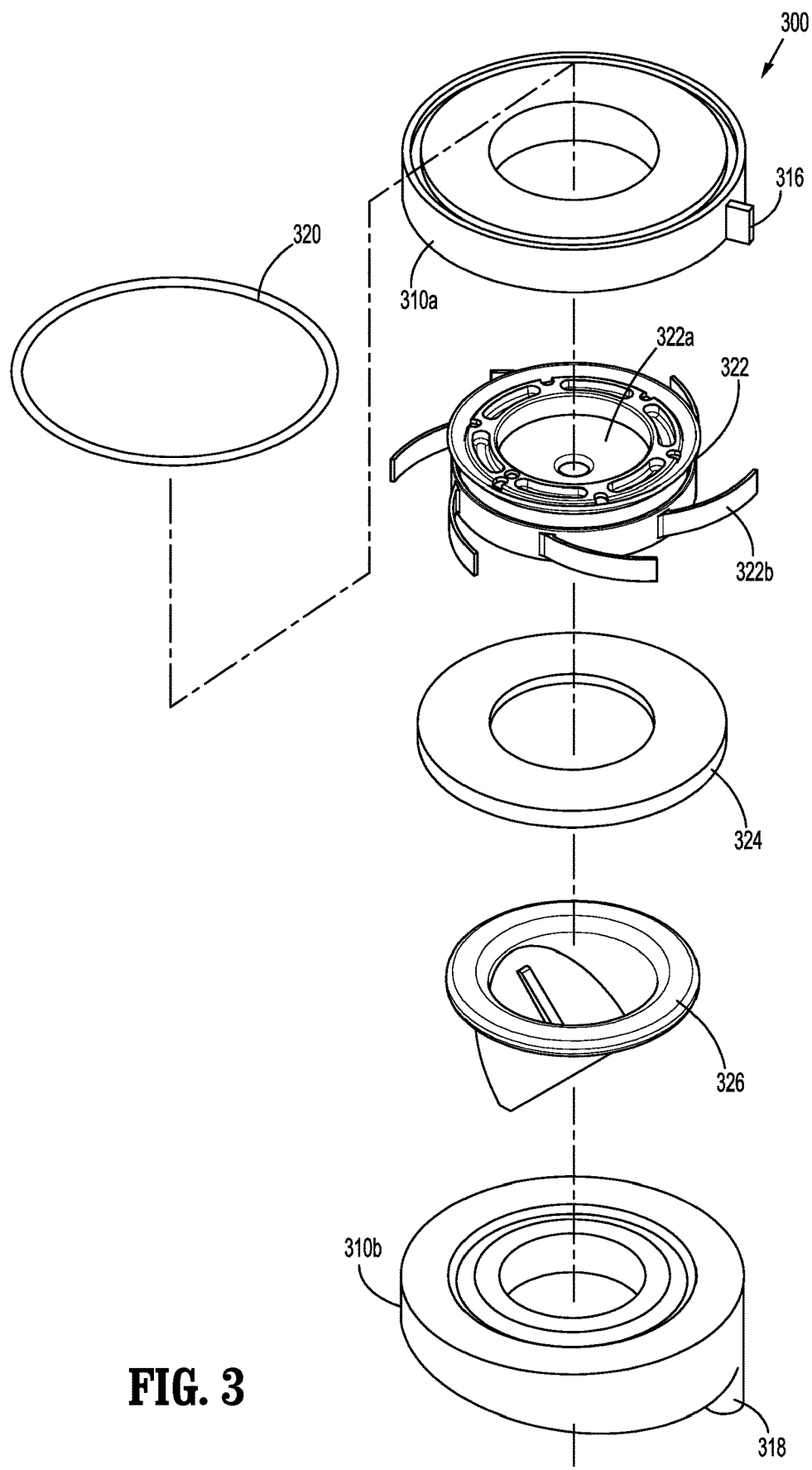
FIG. 3 is a perspective view, with parts separated, of a seal assembly of the surgical port system of FIGS. 1 and 2.
Figure 4:
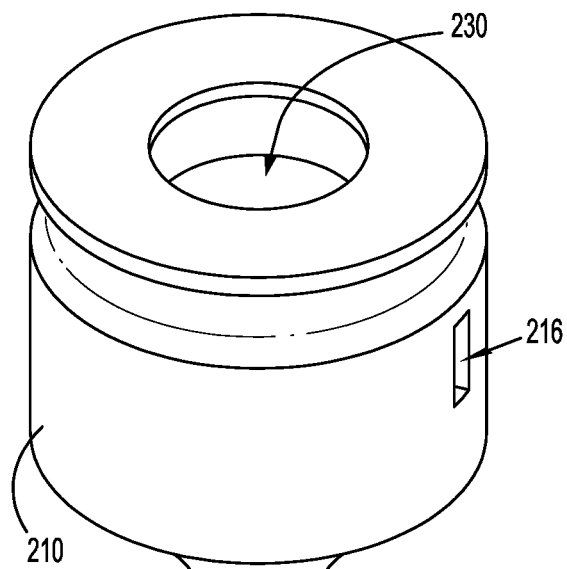
FIG. 4 is a perspective view of a shell of the surgical port system of FIGS. 1 and 2.
Figure 5:
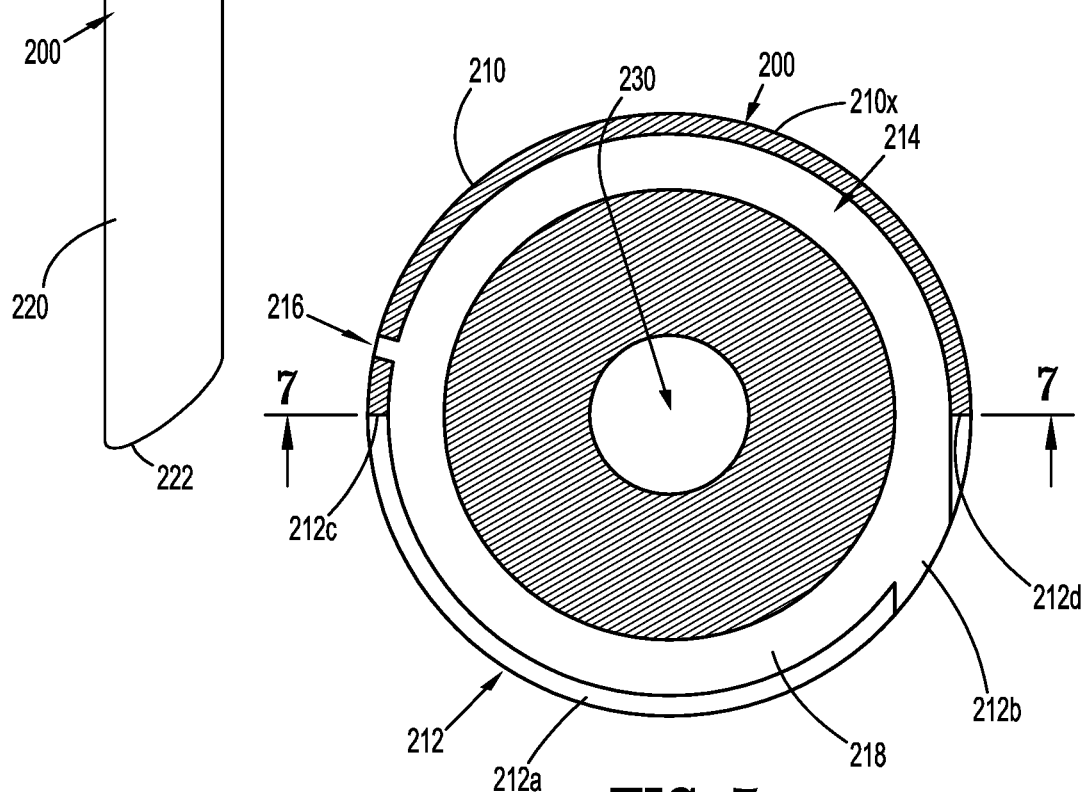
FIG. 5 is an enlarged, cross-sectional view of the shell of FIG. 4 as taken along section line 5-5 shown in FIG. 2.
Figure 6:
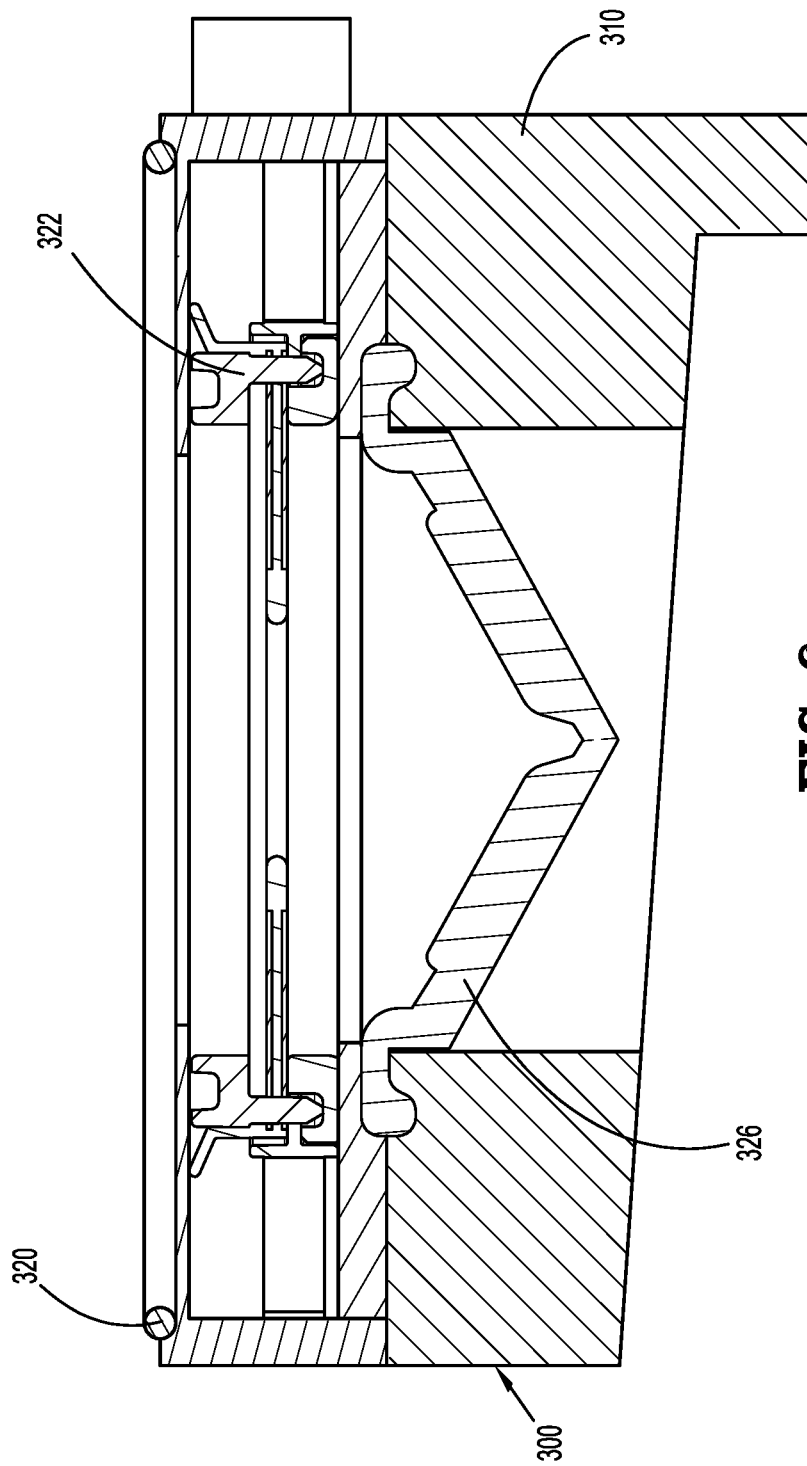
FIG. 6 is an enlarged, cross-sectional view of a seal assembly of the surgical port system of FIGS. 1 and 2 as taken along section line 6-6 shown in FIG. 2.
Figure 7:
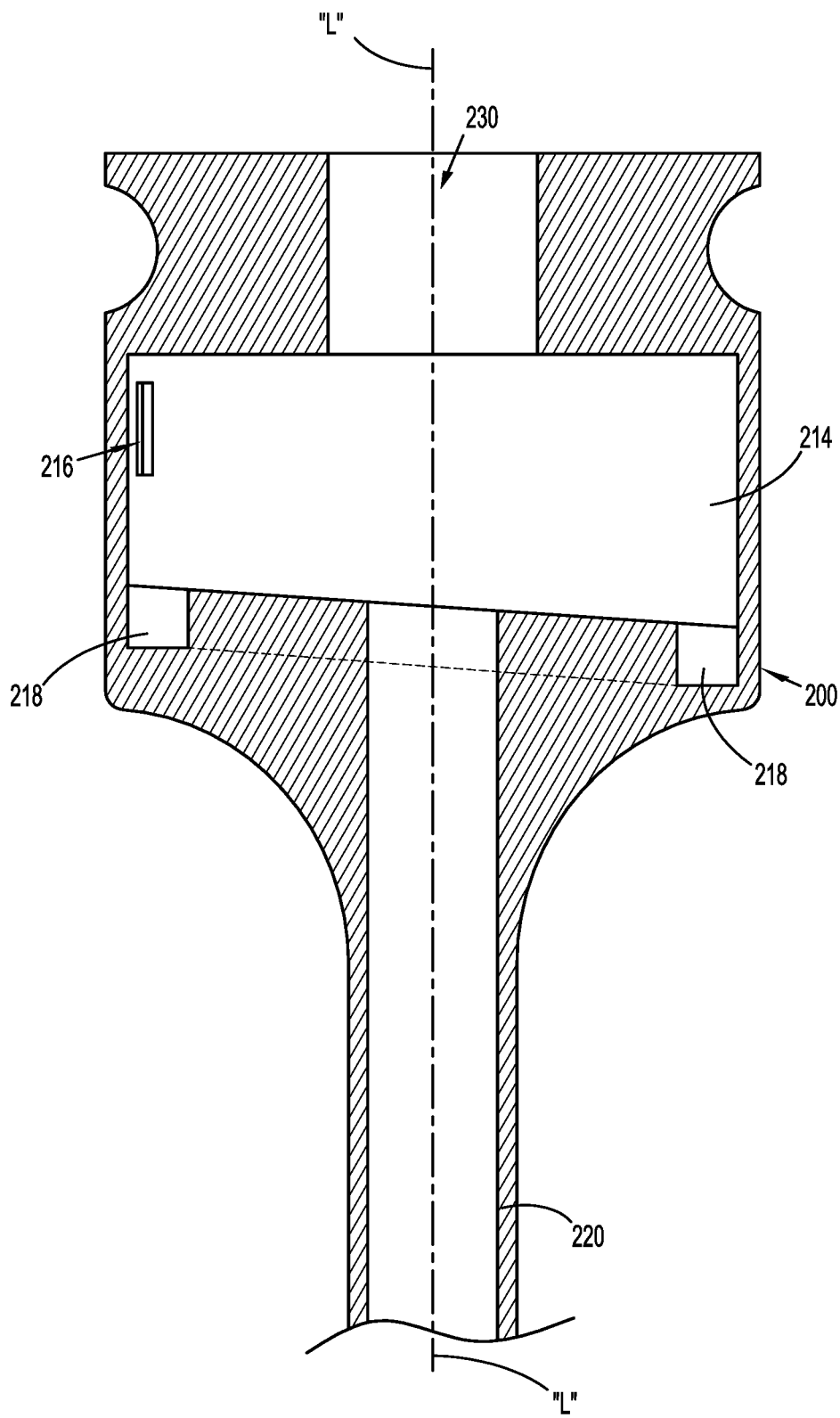
FIG. 7 is an enlarged, cross-sectional view of the shell of FIG. 4 as taken along section line 7-7 shown in FIG. 5.
Figure 8:
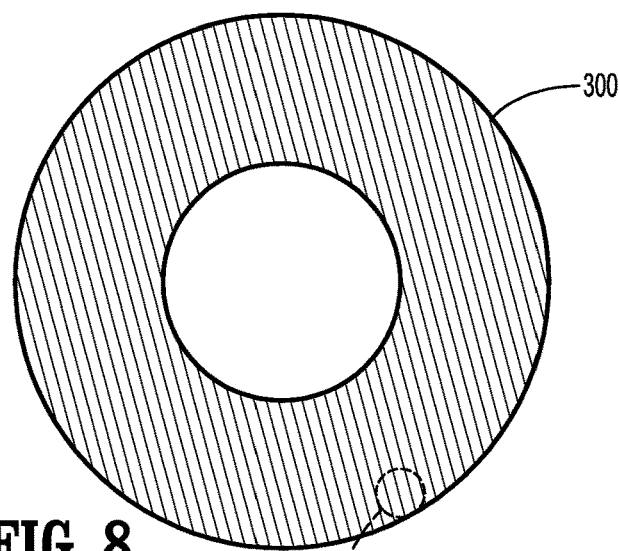
FIG. 8 is an enlarged, cross-sectional view of the seal assembly of FIG. 3 as taken along section line 8-8 shown in FIG. 2.
Figure 9:
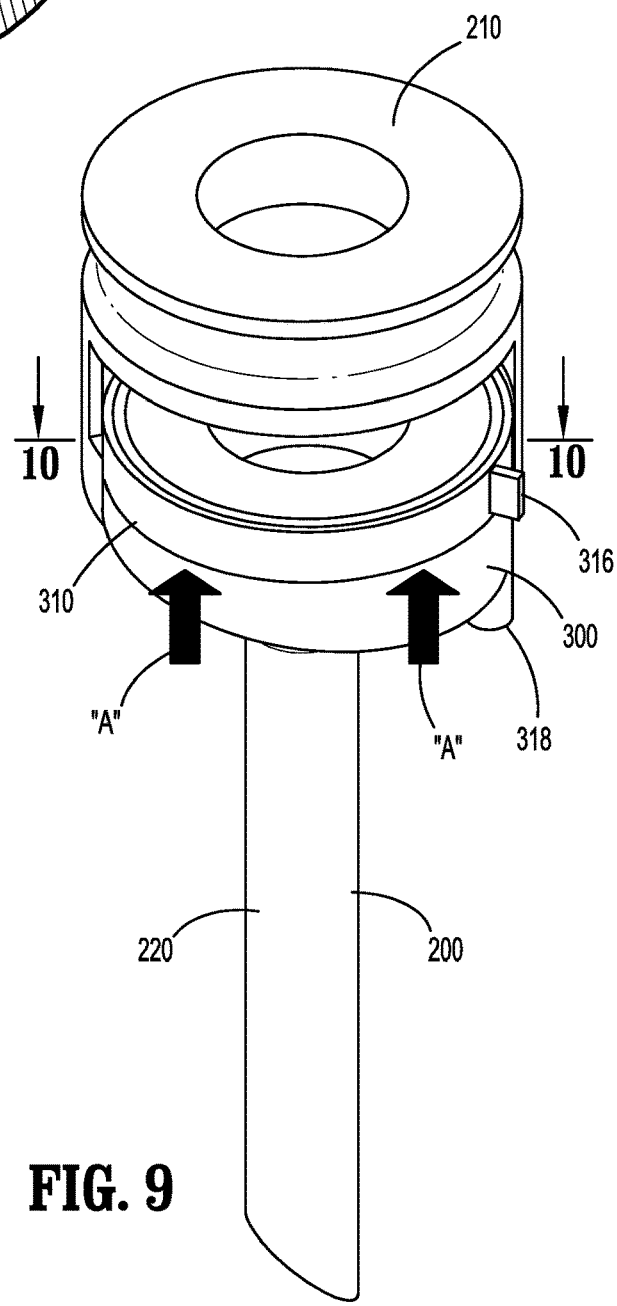
Figure 10:
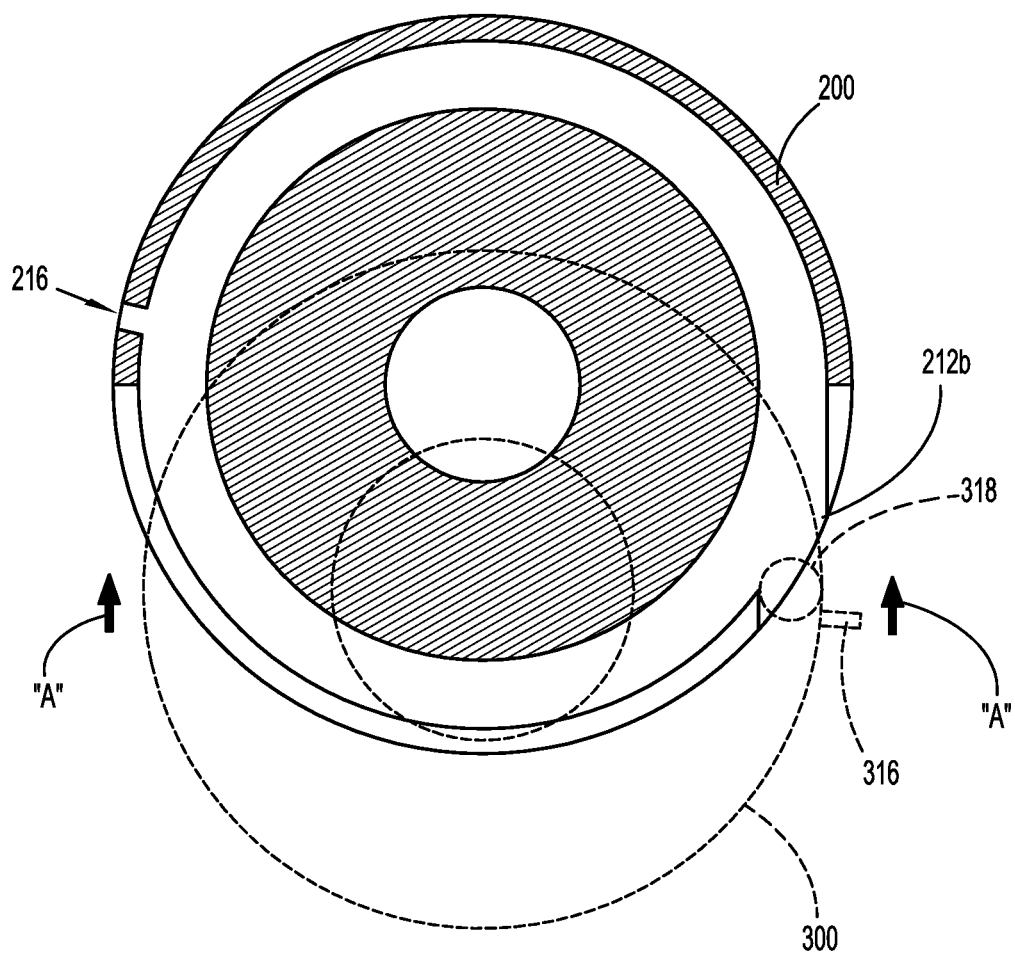
Figure 14:
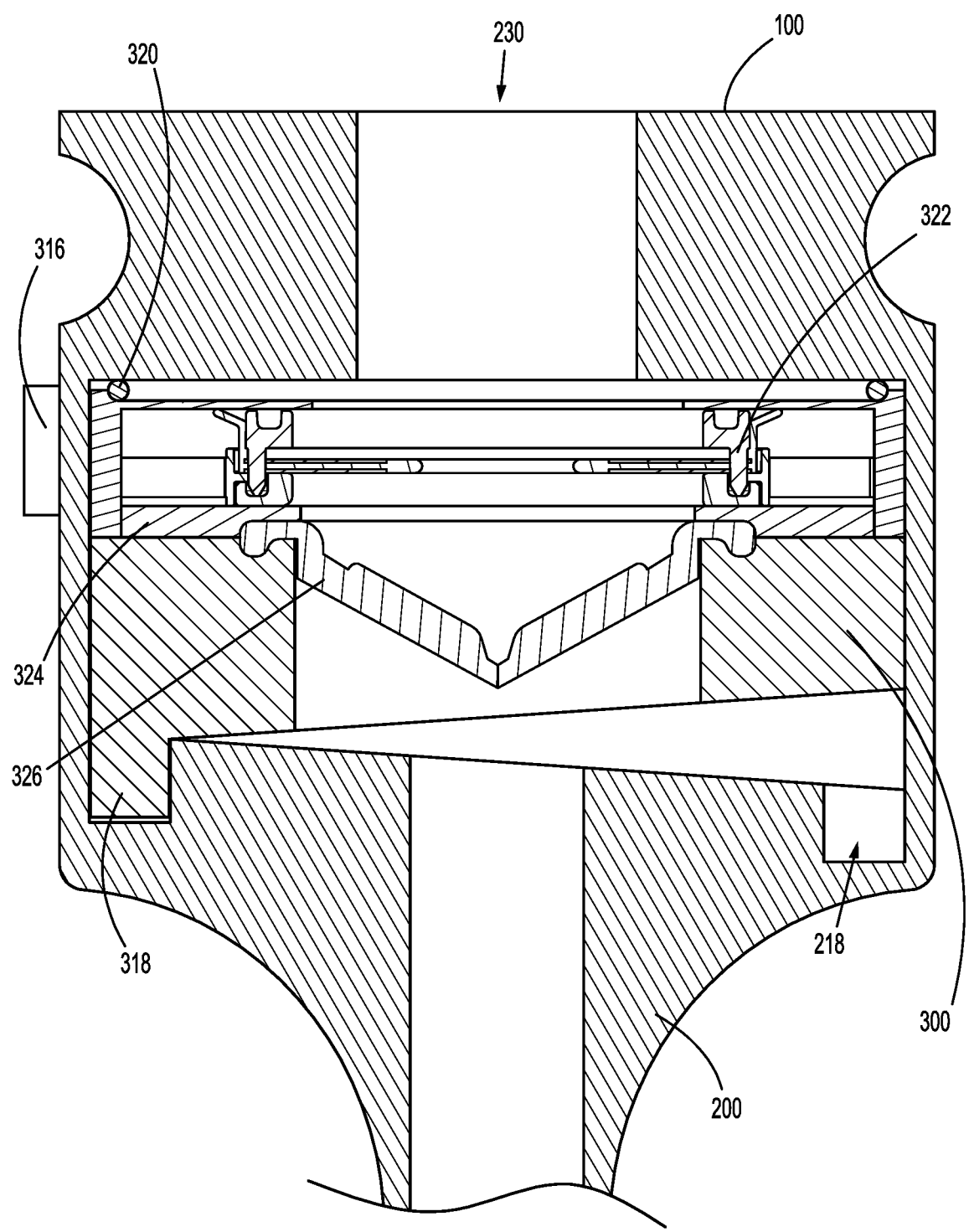
FIG. 14 is an enlarged, cross-sectional view of a trailing end portion of the surgical port system of FIGS. 1 and 2 as taken along section line 14-14 shown in FIG. 12.

As seen in FIG. 3, seal housing 310 of seal assembly 300 supports a floating seal 322 and a duckbill seal 326 that are separated by a disc 324. In embodiments, disc 324 may be integral with the seal housing 310. In some embodiments, floating seal 322 can be positioned on duckbill seal 326. Floating seal 322 includes a septum seal 322a and a plurality of resilient fingers 322b extending radially outward from floating seal 322 at spaced-apart positions about floating seal 322 to enable floating seal 322 to float within seal housing 310.

Referring to FIGS. 9-14, seal assembly 300 can be inserted into housing 210 of shell 200 (e.g., laterally slid into) when features of the seal assembly 300 are aligned with window 212 of shell 200, as indicated by arrows "A". For example, when tooth 318 of seal housing 310 is aligned with tooth gap 212b of shell 200, seal assembly 300 can be received through window 212 and into inner cavity 214 of shell 200 so that central longitudinal axes of seal assembly 300 and shell 200 are aligned with one another, as seen in FIG. 11. With seal assembly 300 seated within inner cavity 214, seal assembly 300 can be rotated (e.g., manually by a clinician) about longitudinal axis "L" so that tooth 318 of seal assembly 300 cams along keyed track 218 of shell 200 as detent 316 of seal assembly 300 cams along angled bottom edge 212a of shell 200 that defines window 212 of shell 200, as indicated by arrows "B." Such camming movement of seal assembly 300 relative to shell 200 causes seal assembly 300 to rotate upwardly along longitudinal axis so that detent 316 of seal assembly 300 can snap-fit into detent slot 216 of shell 200 to rotationally and longitudinal fix seal assembly 300 to shell 200 for sealing surgical instrumentation passed through surgical port assembly 300 (e.g., seal and lock). With seal assembly 300 secured to shell 200, surgical port assembly 300 can be utilized to provide access to, for example, inner body cavities such as the abdominal cavity of a patient. With this configuration of surgical port assembly 300, torque applied to surgical port assembly 300, such as by a robotic system attached thereto (not shown), is received through shell 200 while bypassing seal assembly 300, reducing risk of failure.

Seal assembly 300 can be removed from shell 200, for example, after use of surgical port assembly 300, by actuating (e.g., depressing) detent 316, through detent slot 216 into inner cavity 214 of shell 200, and rotating seal assembly 300 until tooth 318 of seal assembly 300 is re-aligned with tooth gap 212b of shell 200. Once tooth 318 of seal assembly 300 is aligned with tooth gap 212b of shell 200, seal assembly 300 can be removed from shell 200 and discarded. Shell 200 can then be sterilized as desired and a new seal assembly 300 can be inserted into shell 200, as detailed above, for subsequent use.

As can be appreciated, any of the disclosed components of surgical port assembly 100 may be made from additive manufacturing such as 3D printing.

The various surgical ports disclosed herein may also be configured for use with robotic surgical systems, and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Pat. No. 8,828,023, and PCT Application Publication No. WO2016/025132, the entire contents of each of which are incorporated by reference herein.

For a more detailed description of similar surgical ports, one or more components of which can be included with the disclosed embodiments, reference can be made to U.S. Pat. No. 5,807,338, filed Oct. 20, 1995 and U.S. Pat. No. 5,603,702, filed on Aug. 8, 1994, the entire contents of each of which are incorporated by reference herein.

Persons skilled in the art will understand that the structures and methods specifically described herein and illustrated in the accompanying figures are non-limiting exemplary embodiments, and that the description, disclosure, and figures should be construed merely as exemplary of particular embodiments. It is to be understood, therefore, that this disclosure is not limited to the precise embodiments described, and that various other changes and modifications may be effected by one skilled in the art without departing from the scope or spirit of this disclosure. Additionally, it is envisioned that the elements and features illustrated or described in connection with one exemplary embodiment may be combined with the elements and features of another without departing from the scope of this disclosure, and that such modifications and variations are also intended to be included within the scope of this disclosure. Indeed, any combination of any of the disclosed elements and features is within the scope of this disclosure. Accordingly, the subject matter of this disclosure is not to be limited by what has been particularly shown and described.

What is claimed is:

1. A surgical port, comprising:
   a shell having a housing and a cannula extending from the housing, the housing having a sidewall defining a window therethrough; and
   a seal assembly having an angled bottom surface and being selectively laterally receivable into the housing of the shell through the window of the housing from an external position, the housing of the shell having an annular keyed track that urges the seal assembly from a first position in which the angled bottom surface of the seal assembly is sloped in the same direction as the annular keyed track to a second position in which the angled bottom surface of the seal assembly is sloped in a different direction than the annular keyed track.

2. The surgical port of claim 1, wherein the shell secures the seal assembly in the housing when the seal assembly is disposed in the second position.

3. The surgical port of claim 2, wherein the seal assembly is selectively removable from the shell when the seal assembly is moved from the second position, where the seal assembly is secured to the shell, to the first position, where the seal assembly is laterally removable through the window.

4. The surgical port of claim 1, wherein the seal assembly includes a first seal having a duckbill configuration and a second seal having a configuration that is different than the duckbill configuration.

5. The surgical port of claim 4, wherein the second seal has a floating seal configuration.

6. The surgical port of claim 1, wherein the window is angled relative to the housing, the window including an angled bottom edge, a top edge, a first side edge and a second side edge, the first and second side edges connecting the angled bottom edge to the top edge.

7. The surgical port of claim 6, wherein the window includes a tooth gap disposed between the angled bottom edge and the second side edge.

8. The surgical port of claim 7, wherein the seal assembly includes a tooth depending from the angled bottom surface of the seal assembly, the tooth receivable through the tooth gap when the seal assembly is laterally slid into the window.

9. The surgical port of claim 8, wherein the angled bottom surface of the seal assembly is vertically spaced apart from the annular keyed track when the seal assembly is disposed in the second position.

10. The surgical port of claim 1, wherein the window includes a tooth gap, wherein the seal assembly is keyed to the tooth gap to enable the seal assembly to be laterally received through the window.

11. The surgical port of claim 1, wherein the seal assembly includes a tooth depending from the angled bottom surface of the seal assembly, the tooth receivable through a tooth gap when the seal assembly is laterally slid into the window, and wherein the tooth cams along the annular keyed track to move the seal assembly from the first position to the second position.

12. The surgical port of claim 1, wherein the angled bottom surface of the seal assembly is vertically spaced apart from the track when the seal assembly is disposed in the second position.

* * * * *